United States Patent [19]

Heise et al.

[11] 4,269,989

[45] May 26, 1981

[54] PROCESS FOR THE PREPARATION OF BENZIMIDAZOLONE-(2)

[75] Inventors: Hartmut Heise, Bad Soden am Taunus; Ernst Hille, Kelkheim; Reinhard Wagner, Wiesbaden; Kurt Kümmerle, Kelkheim, all of Fed. Rep. of Germany

[73] Assignee: Hoechst Aktiengesellschaft, Frankfurt am Main, Fed. Rep. of Germany

[21] Appl. No.: 105,106

[22] Filed: Dec. 19, 1979

[30] Foreign Application Priority Data

Dec. 21, 1978 [DE] Fed. Rep. of Germany ....... 2855226

[51] Int. Cl.² ............................................ C07D 235/26
[52] U.S. Cl. ..................................................... 548/305
[58] Field of Search ......................................... 548/305

[56] References Cited

U.S. PATENT DOCUMENTS 4,138,568  2/1979  Hari et al. ............................. 548/305

FOREIGN PATENT DOCUMENTS 2113192  5/1972  France ...................................... 548/305
811692  4/1959  United Kingdom .

OTHER PUBLICATIONS

Ullmanns Encyklopedie der Technischen Chemie, 3rd Ed., vol. 8, p. 380, (Evidentiary).

Primary Examiner—Henry R. Jiles
Assistant Examiner—Bernard Dentz
Attorney, Agent, or Firm—Curtis, Morris & Safford

[57] ABSTRACT

Benzimidazolone-(2) is obtained in good yield and high purity when o-phenylene diamine is condensed with urea in water at a pH of 4 to 9 and a temperature above 90° C.

13 Claims, No Drawings

PROCESS FOR THE PREPARATION OF BENZIMIDAZOLONE-(2)

It is known from German Pat. No. 2,052,026 to react ophenylene diamine with an excess amount of urea in water at a temperature of 90° to 160° C. to give benzimidazolone-(2). As compared to other known processes carried out in other solvents or in the melt and to those using phosgene or isocyanates, the reaction with urea in water as the reaction medium offers a series of advantages. On the other hand, the reaction at temperatures above the boiling point necessitates pressure-resistant vessels and special measures against corrosion by the hot alkaline reaction medium formed by the partial decomposition of the urea.

It has now been found that benzimidazolone-(2) can be prepared in an especially advantageous manner by heating o-phenylene diamine and urea in water to a temperature of at least 90° C., preferably at least 100° C., when the reaction is carried out in a pH range of from 4 to 9, preferably 4 to 8 and more preferably 4.5 to 7.

Surprisingly, the process according to the invention need not be carried out under pressure as, at a temperature of from 90° C. to the boiling point of the reaction mixture, high yields are obtained. A further advantage resides in the fact that only a very small excess of urea is required, preferably up to 1.5 mols for each mol of o-phenylene diamine. This fact is extremely surprising as it is known from "Ullmanns Enzyklopädie der technischen Chemie," 3rd edition, volume 8, page 380, that boiling of urea with alkalis or acids involves its decomposition into ammonia and carbon dioxide.

Attainment of the pH of 4 to 9 according to the invention is effected with acids. In principle, any acid can be used provided that it does not undergo undesired secondary reactions with the reaction components. It proved advantageous to use strong mineral acids such as phosphoric acid, especially hydrochloric acid, or sulfuric acid.

By adding the acid, the ammonia set free is bound in salt form whereby the boiling temperature is increased to about 105° C. so that a pressure-resistant vessel can be dispensed with. Furthermore it is thus easier to determine the degree of conversion at any moment of the reaction by taking samples and to control, for example, the yield in dependence on the urea addition or acid addition.

According to a preferred embodiment of the process of the invention, the reaction vessel is first charged with the o-phenylene diamine and part of the urea and the remainder of the urea and the acid are then added simultaneously. When proceeding in this manner, the initially charged amount of urea is advantageously less than that stoichiometrically required.

According to another preferred embodiment, o-phenylene diamine and water are first introduced into the reaction vessel and urea and acid are then metered in. In each case, one reaction component can be added continuously or discontinuously.

Towards the end of the reaction the pH is preferably adjusted to a value exceeding 5, more preferably over 6, since in this manner the purity and the crystal structure of the final product are favorably influenced.

The o-phenylene-diamine can be used in solid form or in the form of an aqueous solution, for example as obtained in the reduction of o-nitraniline.

Because of the o-phenylene diamine being sensitive to oxidation, the reaction should be carried out with the exclusion of oxygen. Hence, the reaction is preferably carried out under an inert gas, preferably carbon dioxide or nitrogen. Instead of the inert gas or in addition thereto, a suitable reducing agent may be added to the reaction mixture, for example sodium dithionite, sodium sulfite or sodium hydrogen sulfite.

The process product is obtained in a high purity and can be used without reprecipitation or recrystallization as intermediate for the manufacture of dyestuffs and pigments.

The following examples illustrate the invention, the parts and percentages being by weight unless otherwise stated.

EXAMPLE 1

An enamel vessel is charged under nitrogen with 2000 parts of drinking water, 700 parts of o-phenylene diamine and 300 parts of urea and the mixture is heated to 100°–105° C. Next, 95% sulfuric acid is added in an amount to maintain the pH in the range of from 5 to 6. A further 100 parts of urea are added after 3 and 6 hours each, while the pH is still maintained between 5 and 6.

A sample is taken and the content of unreacted o-phenylene diamine is determined by titration. As soon as less than 0.2% of the amine is found, the mixture is neutralized with lye and stirring is continued for a further hour. The reaction product is separated on a suction filter and washed with warm water until it is free from salt. Yield: 834 parts or 96% of the theory. Melting point: 314°–315° C.

In the thin layer chromatogram no impurities are found in the product.

EXAMPLE 2

The reaction is carried out as specified in Example 1 with the exception that 40 parts of sodium dithionite are added with the first portion of urea and each time another 15 parts of sodium dithionite are added with the two other urea portions. Yield and melting point are the same as in Example 1.

The products obtaining according to Examples 1 and 2 differ in quality. An approximately 30% solution of the product of Example 1, prepared with dilute sodium hydroxide solution, leaves on a filter paper some black brownish particles of a minor precipitate whereas such a precipitate is substantially not present in the product of Example 2. When high quality products are intended the formation of such dark colored by-products is undesired.

EXAMPLE 3

The vessel is charged with the same amounts of drinking water and o-phenylene diamine as used in Example 1, the mixture is heated and by means of a dosing screw scavenged with nitrogen and, 450 parts of urea are added over a period of about 6 hours. To avoid oxidation reactions, it proved advantageous to add up to 30 parts of sodium dithionite to the urea.

At the same time sulfuric acid is added in an amount sufficient to maintain the pH in the range of from 5 to 6.

When the addition is complete, samples are taken as described above to check whether the reaction is terminated and, when it is, the reaction mixture is worked up as described in Example 1. Yields from 94 to 97% are obtained. The product has the same melting point as in Example 1.

We claim:

1. In a process for the preparation of benzimidazolone-(2) by heating o-phenylenediamine and an excess of urea in water to a temperature of at least 90° C., the improvement comprising heating o-phenylenediamine and an excess amount of urea, the molar ratio of urea to o-phenylenediamine being up to 1.5:1, and maintaining the pH in a range of from 4 to 9 throughout the reaction.

2. A process as claimed in claim 1, wherein the pH is of from 4 to 8.

3. A process as claimed in claim 1, wherein the pH is of from 4.5 to 7.

4. A process as claimed in claim 1, wherein the reaction temperature is at least 100° C.

5. A process as claimed in claim 1, wherein the reaction is performed without applying pressure.

6. A process as claimed in claim 1, wherein o-phenylene diamine and part of the urea are introduced into a reaction vessel and further amounts of urea and the acid for maintaining said pH range are added during the reaction.

7. A process as claimed in claim 1, wherein at the beginning of the reaction less than the stoichiometric amount of urea is present.

8. A process as claimed in claim 1, wherein o-phenylene diamine and water are introduced into a reaction vessel and urea and the acid for maintaining said pH range are added in the course of the reaction.

9. A process as claimed in claim 1, wherein at the end of the reaction the pH is adjusted to above 5.

10. A process as claimed in claim 1, wherein at the end of the reaction the pH is adjusted to above 6.

11. A process as claimed in claim 1, wherein the reaction is performed under exclusion of oxygen.

12. A process as claimed in claim 1, wherein a reducing agent is added to the reaction mixture.

13. A process as claimed in claim 12, wherein the reducing agent is an alkali metal dithionite, sulfite or hydrogen sulfite.

* * * * *